US011475788B2

(12) United States Patent
Dolsma et al.

(10) Patent No.: US 11,475,788 B2
(45) Date of Patent: Oct. 18, 2022

(54) METHOD AND SYSTEM FOR EVALUATING AND MONITORING COMPLIANCE USING EMOTION DETECTION

(71) Applicant: Yuen Lee Viola Lam, Hong Kong (HK)

(72) Inventors: Johan Matthijs Dolsma, Hong Kong (HK); Yuen Lee Viola Lam, Hong Kong (HK)

(73) Assignee: Yuen Lee Viola Lam, Hong Kong (HK)

( * ) Notice: Subject to any disclaimer, the term of this patent is extended or adjusted under 35 U.S.C. 154(b) by 964 days.

(21) Appl. No.: 16/313,895

(22) PCT Filed: Jun. 4, 2018

(86) PCT No.: PCT/IB2018/053968
§ 371 (c)(1),
(2) Date: Dec. 28, 2018

(87) PCT Pub. No.: WO2018/229592
PCT Pub. Date: Dec. 20, 2018

(65) Prior Publication Data
US 2019/0228673 A1  Jul. 25, 2019

Related U.S. Application Data

(63) Continuation-in-part of application No. 15/647,272, filed on Jul. 12, 2017, now abandoned.
(Continued)

(51) Int. Cl.
G06F 16/22 (2019.01)
G09B 19/00 (2006.01)
(Continued)

(52) U.S. Cl.
CPC ......... *G09B 19/00* (2013.01); *G06F 16/2246* (2019.01); *G06N 5/04* (2013.01); *G06N 20/00* (2019.01); *G09B 7/04* (2013.01)

(58) Field of Classification Search
CPC .................................................. G06F 16/2246
See application file for complete search history.

(56) References Cited

U.S. PATENT DOCUMENTS 8,401,609 B2 * 3/2013 Deisseroth ........... A61B 5/0059
600/407
9,014,161 B2 * 4/2015 Calo .................... G06F 16/2246
370/449
(Continued)

FOREIGN PATENT DOCUMENTS

CN  106228293 A  12/2016
CN  106919922 A   7/2017
(Continued)

OTHER PUBLICATIONS

International Search Report of PCT/IB2018/053968 dated Sep. 29, 2018.

*Primary Examiner* — Eliyah S. Harper
(74) *Attorney, Agent, or Firm* — Idea Intellectual Limited; Margaret A. Burke; Sam T. Yip

(57) ABSTRACT

A system for administering, evaluating, and monitoring a subject's compliance with task performance requirements within an action programme comprising optical sensors for capturing subject's facial expression, eye movements, point-of-gaze, and head pose of a subject during a compliance evaluation and monitoring session; a domain knowledge data repository comprising concept data entities, each having knowledge and skill content items, and task data entities, each having lecture content material items; a subject module configured to estimate the subject's affective state and cognitive state using the sensory data collected from the
(Continued)

optical sensors; and a trainer module configured to select a task data entity for delivery and presentment to the subject after each completion of a task data entity based on a probability of the subject's understanding of the associated concept data entity's knowledge and skill content items and a probability of the subject achieving a target compliance level.

20 Claims, 7 Drawing Sheets

Related U.S. Application Data

(60) Provisional application No. 62/520,542, filed on Jun. 15, 2017, provisional application No. 62/594,557, filed on Dec. 5, 2017, provisional application No. 62/622,888, filed on Jan. 27, 2018, provisional application No. 62/627,734, filed on Feb. 7, 2018, provisional application No. 62/646,365, filed on Mar. 21, 2018.

(51) Int. Cl.
*G09B 7/04* (2006.01)
*G06N 20/00* (2019.01)
*G06N 5/04* (2006.01)

(56) References Cited

U.S. PATENT DOCUMENTS

| | | | | |
|---|---|---|---|---|
| 9,983,670 | B2* | 5/2018 | Coleman | A61B 5/369 |
| 10,540,502 | B1* | 1/2020 | Joyce | G06F 21/552 |
| 2010/0017001 | A1* | 1/2010 | Leuthardt | G16H 20/10 |
| | | | | 706/54 |
| 2010/0042578 | A1* | 2/2010 | Leuthardt | G16H 10/60 |
| | | | | 706/59 |
| 2010/0081861 | A1* | 4/2010 | Leuthardt | G16H 20/70 |
| | | | | 600/27 |
| 2010/0100036 | A1* | 4/2010 | Leuthardt | G16H 20/70 |
| | | | | 604/65 |
| 2013/0314243 | A1* | 11/2013 | Le | A61B 5/165 |
| | | | | 340/870.01 |
| 2013/0317384 | A1* | 11/2013 | Le | G16H 20/70 |
| | | | | 600/545 |
| 2017/0231560 | A1* | 8/2017 | Hyde | A61B 5/0002 |
| | | | | 340/870.07 |
| 2018/0311572 | A1* | 11/2018 | Pickover | A63F 13/216 |
| 2018/0336317 | A1* | 11/2018 | Carbonell | G06F 40/30 |

FOREIGN PATENT DOCUMENTS

| | | |
|---|---|---|
| IN | 201621001651 A | 7/2016 |
| JP | 2001337590 A | 12/2001 |
| JP | 2002175307 A | 6/2002 |
| KR | 20100011280 A | 2/2010 |
| KR | 20150002181 A | 1/2015 |
| KR | 20160030415 A | 3/2016 |

* cited by examiner

METHOD AND SYSTEM FOR EVALUATING AND MONITORING COMPLIANCE USING EMOTION DETECTION

CROSS-REFERENCES WITH RELATED DOCUMENTS

This application is a national phase entry of International Patent Application no. PCT/IB2018/053968 filed on Jun. 4, 2018 which claims priority to U.S. Patent Application No. 62/520,542 filed 15 Jun. 2017, U.S. patent application Ser. No. 15/647,272 filed 12 Jul. 2017, U.S. Patent Application No. 62/594,557 filed 5 Dec. 2017, U.S. Patent Application No. 62/622,888 filed 27 Jan. 2018, U.S. Patent Application No. 62/627,734 filed 7 Feb. 2018, and U.S. Patent Application No. 62/646,365 filed 21 Mar. 2018; the disclosures of which are incorporated herein by reference in their entirety.

FIELD OF THE INVENTION

The present invention relates generally to methods and systems for providing and delivery of compliance administration and monitoring in the contexts of educational programmes and training, including corporate training, academic tutoring, in-class and out-of-class learnings, medical treatment and health improvement programmes, sport training, fitness and lifestyle programmes, correctional service and rehabilitation programmes, as well as governmental law and regulatory enforcement, and behavioral standards for individuals. Particularly, the present invention relates to methods and systems for administering, evaluating and monitoring compliance with task performance requirements in an action programme.

BACKGROUND OF THE INVENTION

Compliance means conforming to certain task performance specifications as required by an action programme by a subject enrolled therein. Conventional compliance evaluation and monitoring techniques focus on providing one-time testing with clearly defined passing criteria to subjects in an action programme. Many of these conventional techniques focus only on obtaining pass/fail indicators as effectively as possible without any capability for predicting the subject's progress or guiding the subject towards total compliance. Further, these traditional compliance evaluation and monitoring methods often rely on one-time or sparse, at best, manual administrations of tests. This can hardly provide assurance for compliance on a continuous basis.

To address aforementioned issues, it would be desirable to have an intelligent compliance evaluation and monitoring system that models the affective and cognitive states of the subject, assist the compliance officer in providing personalized compliance instructions and questionnaire in guiding the subject toward total compliance, continuously monitoring the subject's task performance and behavior, and minimize overhead activities associated with the compliance programme.

SUMMARY OF THE INVENTION

The present invention provides a method and system for administering, evaluating, and monitoring a subject's compliance with task performance requirements within an action programme using one or more of sensing of the subject's gestures, emotions, and movements, speech and voice recognition, behavior pattern recognition, and quantitative measurements of questionnaire results and task performances. In accordance to various embodiments of the present invention, the subject within the action programme is to perform certain tasks according to performance specifications. In accordance to one embodiment, the method and system evaluate and monitor the compliance of the subject by periodically administering one or more questionnaires and analyzing the subject's responses to the questionnaires; and by continuously monitoring the subject's performance of one or more tasks under performance specification requirements.

In accordance to one aspect of the present invention, the method and system estimates the affective state and cognitive state of the subject by image and/or video capturing and analyzing the subject's facial expression, eye movements, point-of-gaze, and head pose; and physiologic detection, such as tactile pressure exerted on a tactile sensing device, subject's handwriting, tone of voice, and speech clarity during the subject is responding to the questionnaire or during a sampling time window when the subject is performing the task procedure. The image or video capture can be accomplished by using built-in or peripheral cameras in desktop computers, laptop computers, tablet computers, and/or smartphones used by the subject in responding to the questionnaire, and/or other optical sensing devices placed and installed in the environments within which the subject performs the tasks in the action programme. The captured images and/or videos are then analyzed using machine vision techniques. For example, stalled eye movements, out-of-focus point-of-gaze, and a tilted head pose are signals indicating lack of interest and attention toward, and/or lack of knowledge in the subject matters being presented in the questionnaire and task procedural instructions, untruthfulness in answering the questionnaire, or lack of skill/knowledge in the tasks at hands; while a strong tactile pressure detected is a signal indicating anxiety, lack of confidence, and/or frustration in the subject matters being presented in the questionnaire and task procedural instructions or of the tasks at hands; either could represent a tendency of low level of compliance or noncompliance.

In accordance to one embodiment, selected performance data and behavioral data from the subject are also collected in determining the subject's comprehension of and level of engagement in the materials presented in the questionnaires and task procedural instructions for tasks required to be performed in the action programme. These selected performance data and behavioral data include, but not limited to, correctness of answers to questions in the questionnaire, number of successful and unsuccessful attempts, closeness of the subject's answers to model answers, number of toggling between given answer choices, and response speed to questions of certain types, and subject matters. For example, the subject's excessive toggling between given choices and slow response speed in answering a question indicate doubts and hesitations on the answer to the question.

The affective state and cognitive state estimation and performance data are primarily used in gauging the subject's level of compliance with performance specifications of tasks in an action programme. While a single estimation is used in providing a snapshot assessment of the subject's progress toward total compliance in her task performance and prediction of the subject's eventual achievable level of compliance, multiple estimations are used in providing an assessment history and trends of the subject's progress. Furthermore, the estimated affective states and cognitive states of the subject are used in the modeling of the compliance programme in terms of choice of methods of compliance evaluation and monitoring, and instruction delivery and administration.

In accordance to another aspect of the present invention, the method and system provide a mechanism for delivering and managing interactive and adaptive compliance questionnaire and task procedural instructions. The mechanism logically structures the questionnaire and task procedural instructions materials and the delivery mechanism data for evaluating and monitoring compliance in an action programme as Domain Knowledge, and its data are stored in a Domain Knowledge repository. A Domain Knowledge repository comprises one or more Concept objects and one or more Task objects. Each Concept object comprises one or more Knowledge and Skill items. The Knowledge and Skill items are ordered by task performance specification complexity/difficulty/stringency levels, and two or more Knowledge and Skill items can be linked to form a Curriculum. In the case where the present invention is applied in a particular industry or business, a Curriculum defined by the present invention may be the equivalence of the operation manual/standard and there is one-to-one relationship between a Knowledge and Skill item and a task performance specification in the operation manual/standard. The Concept objects can be linked to form a logical tree data structure for used in a Task selection process.

Each Task object has various task procedural instruction materials. Each Task object is associated with one or more Concept objects in a Curriculum. In accordance to one embodiment, a Task object can be classified as: Basic Task, Interactive Task, or Task with an Underlying Cognitive or Expert Model. Each Basic Task comprises one or more operation notes, task procedural instructions, illustrations, test questions and answers designed to assess whether the subject has read all the materials. Each Interactive Task with an Underlying Cognitive or Expert Model comprises one or more task procedures each comprises one or more instructional steps designed to guide the subject in completing the task procedure according to performance specification. Each step provides an answer, common misconceptions, and hints. The steps are in the order designed to follow the delivery flow of a task procedure. This allows a tailored scaffolding (e.g. providing guidance and/or hints) for each task based on a point in a task procedure executed.

In accordance to another aspect of the present invention, the mechanism for delivering and managing interactive and adaptive compliance questionnaires and instructions logically builds on top of the Domain Knowledge two models of operation: Subject Model and Training Model. Under the Subject Model, the system executes each of one or more of the Task objects associated with a Curriculum in a Domain Knowledge in a work session for a subject. During the execution of the Task objects, the system measures the subject's performance and obtain the subject's performance metrics in each Task such as: the numbers of successful and unsuccessful attempts to complete the instructional steps in the Task, number of hints requested, and the time spent in completing the Task. The performance metrics obtained, along with the information of the Task object, such as its specification complexity/difficulty/stringency level, are fed into a logistic regression mathematical model of each Concept object associated with the Task object. This is also called the knowledge trace of the subject, which is the calculation of a probability of the subject achieving a target compliance level in a task associated with the with the task performance specification in the Concept object. The advantages of the Subject Model include that the execution of the Task objects can adapt to the changing ability of the subject. For non-limiting example, following the Subject Model, the system can estimate the compliance level achievable by the subject, estimate how much performance improvement can be expected for a next Task, and provide a prediction of the subject's level of compliance in a future point of time. These data are then used in the Training Model and enable hypothesis testing to make further improvement to the system, evaluate compliance officer quality and compliance questionnaire and task procedural instruction material quality.

Under the Training Model, the system receives the data collected from the execution of the Task objects under the Subject Model and the Domain Knowledge for making decisions on the instruction delivery strategy and providing feedbacks to the subject and compliance officer. Under the Training Model, the system is mainly responsible for executing the followings:

1.) Define the entry point for the first Task. Initially all indicators for Knowledge and Skill items are set to defaults, which are inferred from data in either an application form filled by the subject or compliance officer or an initial assessment of the subject by the compliance officer. Select the sequence of Tasks to execute. To select the next Task, the system's trainer module has to search through a logical tree data structure of Concept objects, locate a Knowledge and Skill with the lowest skill level and then use a question matrix to lookup the corresponding Task items that match the learning traits of the subject. Once selected, the necessary compliance questionnaire and task procedural instruction materials are pulled from the Domain Knowledge, and send to the system's communication module for delivery presentation in the system's communication module user interface.

2.) Provide feedback. While the subject is working on a Task object being executed, the system's trainer module monitors the time spent on each Task step. When a limit is exceeded, feedback is provided as a function of the current affective state of the subject. For example, this can be an encouraging, empathetic, or challenging message selected from a generic list, or it is a dedicated hint from the Domain Knowledge.

3.) Drive the system's pedagogical agent. The system's trainer module matches the current affective state of the subject with the available states in the pedagogical agent. Besides providing the affective state information, text messages can be sent to the system's communication module for rendering the pedagogical agent in a user interface.

4.) Decide when a Concept is mastered. As described earlier, under the Subject Model, the system estimates the probability of the subject achieving a target compliance level in a task associated with the task performance specification materials in each Concept. Based on a predetermined threshold (e.g. 95%), the compliance officer can decide when a Concept is mastered.

In accordance to another aspect of the present invention, the method and system for administering, evaluating, and monitoring a subject's compliance with task performance requirements within an action programme incorporate machine learning techniques that are based on interlinking models of execution comprising: a Domain Model, an Assessment Model, a Learner Model, a Deep Learner Model, one or more Motivational Models, a Transition Model, and a Pedagogical Model. The interlinking models of execution is purposed for driving, inducing, or motivating certain desirable actions, behavior, and/or outcome from the subject. These certain desirable actions and/or outcome can be, as non-limiting examples, mastering certain task procedures, adopting certain desirable behaviors, achieving certain job assignment goals, making certain purchases, and conducting certain commercial activities. Therefore, these interlinking models of execution are also applicable in the fields of corporate training and commercial retailing and trading.

BRIEF DESCRIPTION OF THE DRAWINGS

Embodiments of the invention are described in more detail hereinafter with reference to the drawings, in which.

DETAILED DESCRIPTION

Figure 1:
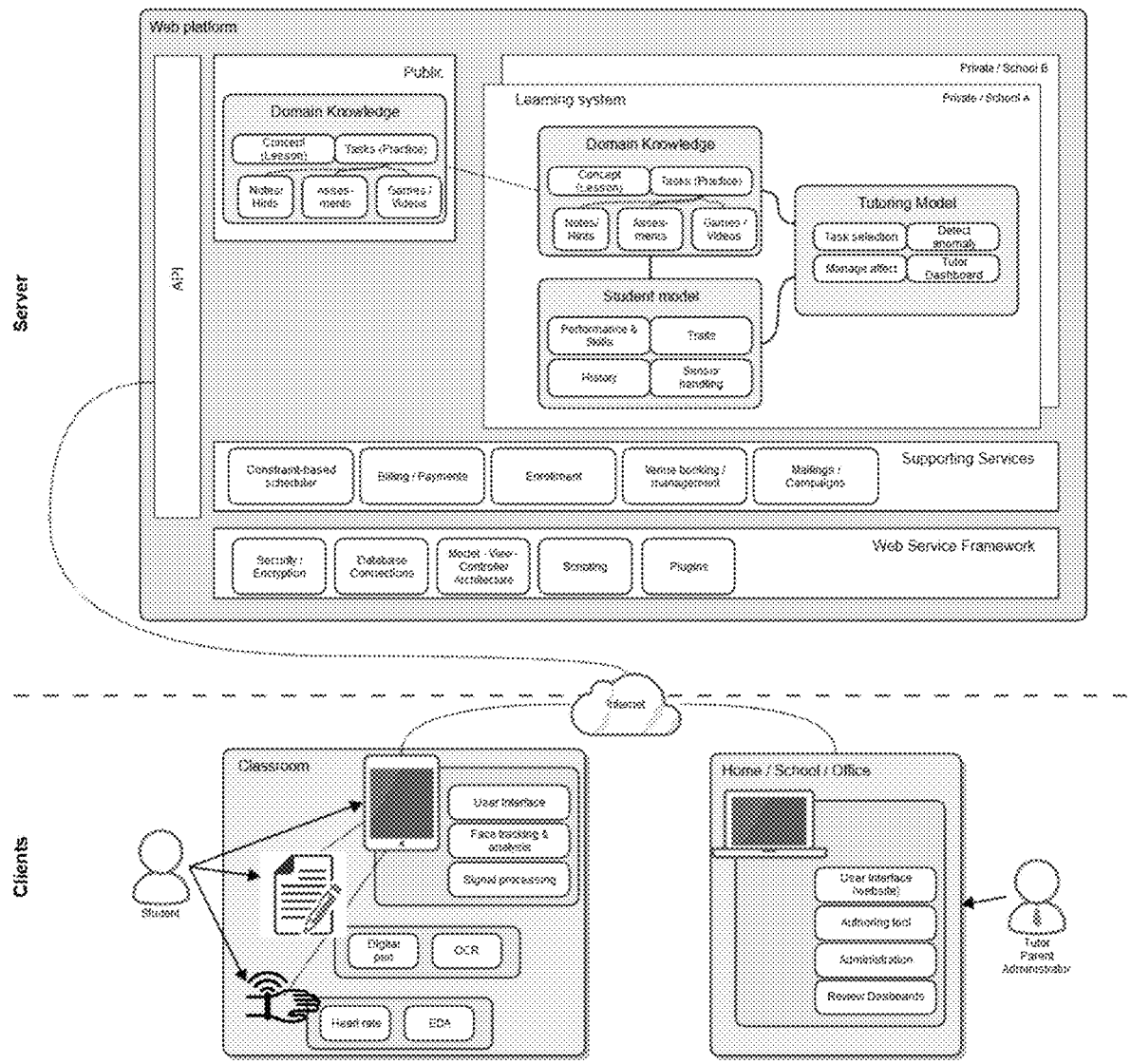
FIG. 1 depicts a schematic diagram of a system for administering, evaluating, and monitoring a subject's compliance with task performance requirements within an action programme in accordance to one embodiment of the present invention.

In the following description, methods and systems for administering, evaluating, and monitoring a subject's compliance with task performance requirements within an action programme and the likes are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

In accordance to various embodiments of the present invention, the method and system for administering, evaluating, and monitoring a subject's compliance with task performance requirements within an action programme use a combination of sensing of the subject's gestures, emotions, and movements, and quantitative measurements of questionnaire results and task performances.

In accordance to one aspect of the present invention, the method and system estimate the affective state and cognitive state of the subject by image and/or video capturing and analyzing the subject's facial expression, eye movements, point-of-gaze, and head pose, and haptic feedback, such as tactile pressure exerted on a tactile sensing, subject's handwriting, tone of voice, and speech clarity during the subject is responding to the questionnaire or during a sampling time window when the subject is performing the task procedure. The image or video capture can be performed by using built-in or peripheral cameras in desktop computers, laptop computers, tablet computers, and/or smartphones used by the subject, and/or other optical sensing devices placed and installed in the environments within which the subject performs the tasks in the action programme. The captured images and/or videos are then analyzed using machine vision techniques. For example, stalled eye movements, out-of-focus point-of-gaze, and a tilted head pose are signals indicating lack of interest and attention, and/or lack of knowledge in the subject matters being presented in questionnaire, untruthfulness in answering the questionnaire, or lack of skill/knowledge in the tasks at hands; while a strong tactile pressure detected is a signal indicating anxiety, lack of confidence, and/or frustration in the subject matters being presented in questionnaire or of the tasks at hands; either could represent a tendency of low level of compliance or noncompliance.

In accordance to one embodiment, selected performance data and behavioral data from the subject are also collected in the affective state and cognitive state estimation. These selected performance data and behavioral data include, but not limited to, number of successful and unsuccessful attempts to task procedural step completions, speed in completing task procedures, correctness of answers to questions in the questionnaire, number of successful and unsuccessful attempts to questions, closeness of the subject's answers to model answers, toggling between given answer choices, and response speed to test questions of certain types, subject matters, and/or task performance specification complexity/difficulty/stringency levels, working steps toward a solution, the subject's handwriting, tone of voice, and speech clarity. For example, the subject's excessive toggling between given choices and slow response speed in answering a test question indicating doubts and hesitations on the answer to the question. The subject's intermediate working steps toward completing a task procedural step are captured for matching with the model solution and in turn provides insight to the subject's understanding of the task procedural instruction and task performance specification materials.

In accordance to various embodiments, the system for administering, evaluating, and monitoring a subject's compliance with task performance requirements within an action programme comprises a sensor handling module implemented by a combination of software and firmware executed in general purposed and specially designed computer processors. The sensor handling module manages the various sensors employed by the system. The sensor handling module is in electrical and/or data communications with various electronic sensing devices including, but not limited to, optical and touch sensing devices; input devices including, but not limited to, keyboard, mouse, pointing device, stylus, and electronic pen; image capturing devices; and cameras.

During the operation of the system, input sensory data are continuously collected at various sampling rates and averages of samples of input sensory data are computed. In order to handle the different sampling rates of different sensing devices, a reference rate is chosen (e.g. 5 Hz). A slower sampling rate input sensory data is interpolated with zero order hold and then sampled at the reference rate. A higher sampling rate input sensory data is subsampled at the reference rate. After the sample rate alignment, a trace of the last few seconds is kept in memory after which the average is calculated. Effectively this produces a moving average of an input sensory data and acts as a low-pass filter to remove noise.

Eye movements, Point-of-Gaze, and Head Pose Detection

In one embodiment, a low-cost optical sensor built-in in a computing device (e.g. subject facing camera in a tablet computer) is used. At a rate of minimal 5 Hz, images are obtained from the sensor. Each image is then processed by face/eye tracking and analysis systems known in the art. The three-dimensional (3D) head orientation is measured in Euler angles (pitch, yaw, and roll). To measure the point-of-gaze, a 3D vector is assumed from the origin of the optical sensor to the center of the pupil of the user, secondly, a 3D vector is determined from the center of the eye-ball to the pupil. These two vectors are then used to calculate the point of gaze. A calibration step helps to compensate for offsets (subject position behind the screen, camera position relative to the screen). Using this data, the planar coordinate of the gaze on the computer screen can be derived.

Facial Expressions and Emotions Determination

In another embodiment, the images and/or videos captured as mentioned above, are processed to identify key landmarks on the face such as eyes, tip of the nose, corners of the mouth. The regions between these landmarks are then analyzed and classified into facial expressions such as: attention, brow furrow, brow raise, cheek raise, chin raise, dimpler (lip corners tightened and pulled inwards), eye closure, eye widen, inner brow raise, jaw drop, lid tighten, lip corner depression, lip press, lip pucker (pushed forward), lip stretch, lip such, mouth open, nose wrinkle, smile, smirk, upper lip raise. These expressions are then mapped, using a lookup table, onto the following emotions: anger, contempt, disgust, engagement (expressiveness), fear, joy, sadness, surprise and valence (both positive as negative nature of the person's experience). Each emotion is encoded as a percentage and output simultaneously.

Physiologic Measurement

In another embodiment, the system comprises a wearable device to measure physiologic parameters not limiting to: heart rate, electro dermal activity (EDA) and skin temperature. This device is linked wirelessly to the client computing device (e.g. tablet computer or laptop computer). The heart rate is derived from observations of the blood volume pulse. The EDA measures skin conductivity as an indicator for sympathetic nervous system arousal. Based on this, features related to stress, engagement, and excitement can be derived. Another approach is to use vision analysis techniques to directly measure the heart rate based on the captured images. This method is based on small changes in light absorption by the veins in the face, when the amount of blood varies due to the heart rate.

Handwriting Analysis

In another embodiment, test answers may be written on a dedicated note paper using a digital pen and receive commands such as 'task procedural step completed'. The written answer is then digitized on the fly and via an intelligent optical character recognition engine, the system can evaluate the content written by the subject and provide any necessary feedback to guide the subject when needed. Studies show that taking longhand notes encourages subjects to process and reframe information, improving the compliance results. Alternatively, embodiments may use OCR after the tasks has been completed. The paper is scanned using a copier and the digitized image is fed to OCR software.

Speech and Voice Recognition and Analysis

In another embodiment, the system comprises one or more voice recording devices for recording the subject's speech during a compliance evaluation and monitoring session. The subject's speech is then digitized on the fly and via an intelligent voice recognition engine, the system can evaluate the content spoken by the subject and provide any necessary feedback to guide the subject when needed. The substantive content of the subject's speech is recognized for verbal commands related to a task procedure and/or verbal answers to questionnaire test questions for further compliance analysis. The subject's voice and speech clarity are recognized as input to the affective state and cognitive state estimation.

Pedagogical Agent-Subject Interaction

As a non-limiting example, a pedagogical agent may be non-human animated character with human traits implemented by a combination of software and/or firmware running in one or more general purposed computer processors and/or specially configured computer processors. It can display the basic emotions by selecting from a set of animations (e.g. animated GIFs), or by using scripted geometric transformation on a static image displayed to the subject in a user interface. Another method is to use SVG based animations. The animation can be annotated with text messages (e.g. displayed in a balloon next to the animation). The text messages are generated by and received from the trainer module of the system. The subject's responses to the pedagogical agent are received by the system for estimating the subject's affective state.

The affective state and cognitive state estimation and performance data are primarily used in gauging the subject's level of compliance with performance specifications of tasks in an action programme. While a single estimation is used in providing a snapshot assessment of the subject's progress toward total compliance in her task performance and prediction of the subject's eventual achievable level of compliance, multiple estimations are used in providing an assessment history and trends of the subject's progress. Furthermore, the estimated affective states and cognitive states of the subject are used in the modeling of the compliance programme in terms of choice of methods of compliance evaluation and monitoring, and instruction delivery and administration.

Domain Knowledge

Figure 5:
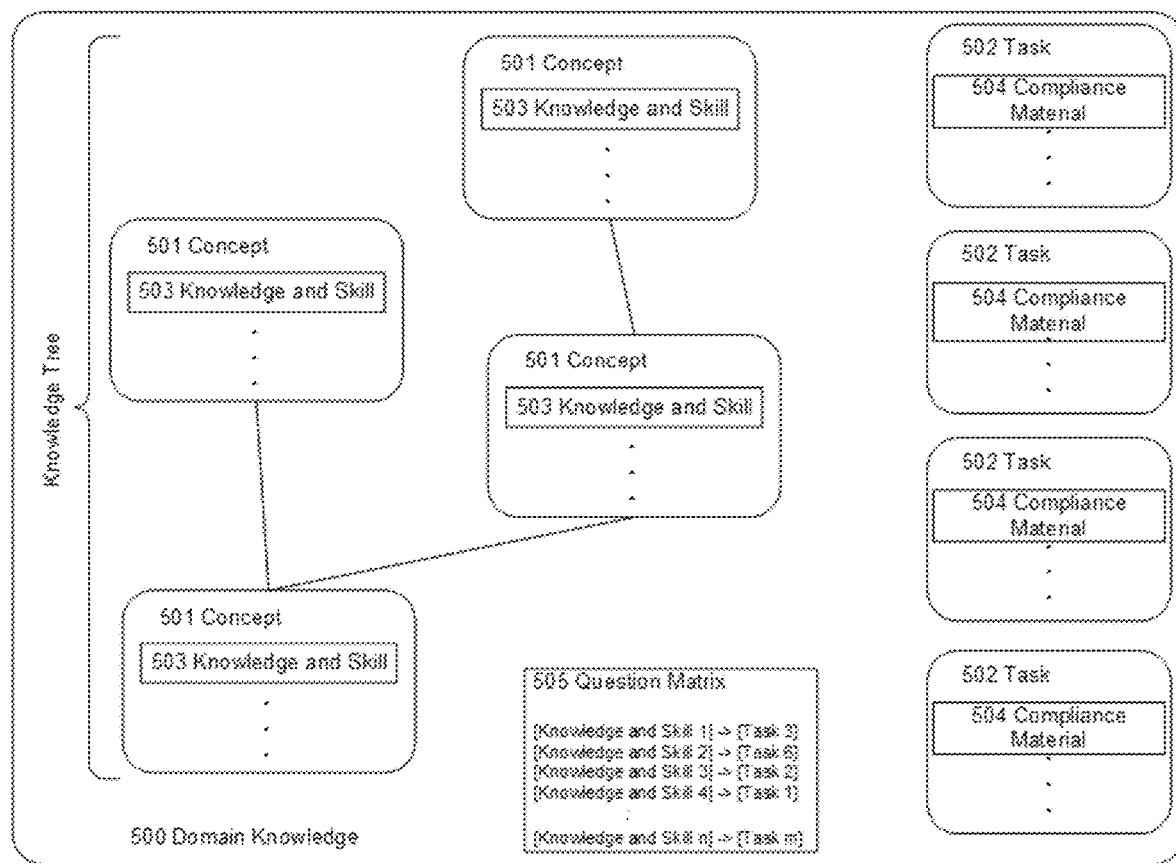
FIG. 5 illustrates a logical data structure used by the system in accordance to one embodiment of the present invention.

Referring to FIG. 5. In accordance to one aspect of the present invention, the method and system logically structure the compliance questionnaire and task procedural instruction materials, and the delivery mechanism in a compliance programme as Domain Knowledge 500. A Domain Knowledge 500 comprises one or more Concept objects 501 and one or more Task objects 502. Each Concept object 501 comprises one or more Knowledge and Skill items 503. The Knowledge and Skill items 503 are ordered by task performance specification complexity/difficulty/stringency levels, and two or more Concept objects 501 can be grouped to form a Curriculum. In the case where the present invention is applied in a particular industry or business, a Curriculum defined by the present invention may be the equivalence of the operation manual/standard and there is one-to-one relationship between a Knowledge and Skill item and a task performance specification in the operation manual/standard. The Concept objects can be linked to form a logical tree data structure (Knowledge Tree) such that Concept objects having Knowledge and Skill items that are fundamental and/or basic in a topic are represented by nodes closer to the root of the logical tree and Concept objects having Knowledge and Skill items that are more advance and branches of some common fundamental and/or basic Knowledge and Skill items are represented by nodes higher up in different branches of the logical tree.

Each Task object 502 has various compliance questionnaire and task procedural instruction content materials 504, and is associated with one or more Concept objects 501 in a Curriculum. The associations are recorded and can be looked up in a question matrix 505. In accordance to one embodiment, a Task object 502 can be classified as: Basic Task, Interactive Task, or Task with an Underlying Cognitive or Expert Model. Each Basic Task comprises one or more operation notes, task procedural instructions (e.g. video clips and other multi-media content), test questions and answers designed to assess whether the subject has read all the materials. Each Interactive Task with an Underlying Cognitive or Expert Model comprises one or more problem-solving exercises each comprises one or more steps designed to guide the subject in deriving the solutions to problems. Each step provides an answer, common misconceptions, and hints. The steps are in the order designed to follow the delivery flow of a task procedure. This allows a tailored scaffolding (e.g. providing guidance and/or hints) for each task based on a point in a task procedure executed.

In accordance to various embodiments, a Task object gathers a set of compliance questionnaire and task procedural instruction materials (e.g. operation notes and illustrations) relevant in the achievement of a compliance level. In addition to the aforementioned classification, a Task can be one of the following types:

1.) Reading Task: operation notes or illustrations to introduce a new topic without grading, required to be completed before proceeding to a Practice Task is allowed;
2.) Practice Task: a set of questions from one topic to practice on questions from a new topic until a threshold is reached (e.g. five consecutive successful attempts without hints, or achieve an understanding level of 60% or more);
3.) Mastery Challenge Task: selected questions from multiple topics to let the subject achieves mastery (achieve an understanding level of 95% or more) on a topic, and may include pauses to promote retention of knowledge (e.g. review opportunities for the subjects); or
4.) Group Task: a set of questions, problem sets, and/or problem-solving exercises designed for peer challenges to facilitate more engagement from multiple subjects in a focus group, may be ungraded.

In accordance to one embodiment, the Domain Knowledge, its constituent Task objects and Concept objects, Knowledge and Skill items and Curriculums contained in each Concept object, operation notes, illustrations, test questions and answers in each Task object are data entities stored a relational database accessible by the system (a Domain Knowledge repository). One or more of Domain Knowledge repositories may reside in third-party systems accessible by the system for administering, evaluating, and monitoring a subject's compliance with task performance requirements within an action programme.

In accordance to another aspect of the present invention, the mechanism for delivering and managing interactive and adaptive compliance questionnaires and task procedural instructions logically builds on top of the Domain Knowledge two models of operation: Subject Model and Training Model.

Subject Model

Under the Subject Model, the system executes each of one or more of the Task objects associated with a Curriculum in a Domain Knowledge for a subject. During the execution of the Task objects, the system measures the subject's performance and obtain the subject's performance metrics in each Task such as: the numbers of successful and unsuccessful attempts to questions in the Task, number of hints requested, and the time spent in completing the Task. The performance metrics obtained, along with the information of the Task object, such as its specification complexity/difficulty/stringency level, are fed into a logistic regression mathematical model of each Concept object associated with the Task object. This is also called the knowledge trace of the subject, which is the calculation of the probability of the subject achieving a target compliance level in a task associated with the Concept object. In one embodiment, the calculation of a probability of achieving a target compliance level uses a time-based moving average of subject's answer scores to questions in the questionnaires with lesser weight on older attempts, the number of successful attempts, number of failed attempts, success rate (successful attempts over total attempts), time spent, and task performance specification complexity/difficulty/stringency level. In another embodiment, the calculation of a probability of achieving a target compliance level uses a time-based moving average of subject's completion of task procedural steps with lesser weight on older attempts, the number of successful attempts, number of failed attempts, success rate (successful attempts over total attempts), time spent, and task performance specification complexity/difficulty/stringency level.

Figure 4:
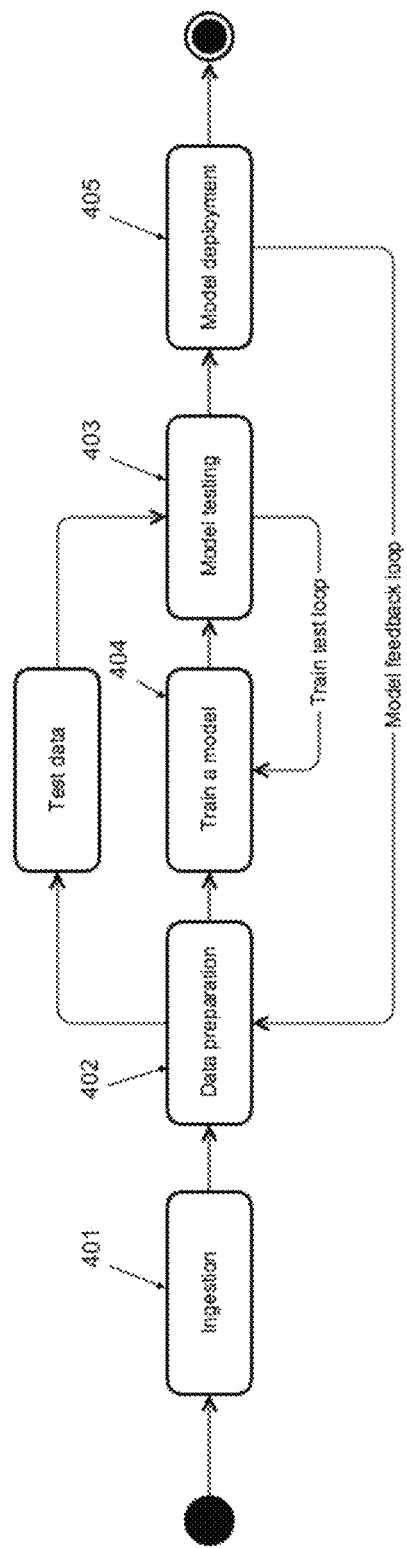
FIG. 4 depicts a flow diagram of an iterative machine learning workflow used by the system in calculating a probability of achieving a target compliance level by the subject.

In one embodiment, the system calculates the probability of the subject achieving a target compliance level in a task associated with the task performance specification in the Concept object using an iterative machine learning workflow to fit mathematical models on to the collected data (subject's performance metrics and information of the Task) including, but not limited to, a time-based moving average of subject's answer scores to questions in the questionnaires with lesser weight on older attempts, the number of successful attempts, number of failed attempts, success rate (successful attempts over total attempts), time spent, topic difficulty, and question difficulty. FIG. 4 depicts a flow diagram of the aforesaid iterative machine learning workflow. In this exemplary embodiment, data is collected (401), validated and cleansed (402); then the validated and cleansed data is used in attempting to fit a mathematical model (403); the mathematical model is trained iteratively (404) in a loop until the validated and cleansed data fit the mathematical model; then the mathematical model is deployed (405) to obtain the probability of the subject achieving a target compliance level in a task associated with the task performance specification in the Concept object; the fitted mathematical model is also looped back to and used in the step of validating and cleansing of the collected data.

The knowledge trace of the subject is used by the system in driving Task compliance questionnaire and task procedural instruction material items selection, driving Task object selection, and driving compliance questionnaire and task procedural instruction material ranking. The advantages of the Subject Model include that the execution of the Task objects can adapt to the changing ability of the subject. For non-limiting example, under the Subject Model the system can estimate the compliance level achievable by the subject, estimate how much performance improvement can be expected for the next Task, and provide a prediction of the subject's level of compliance in a future point of time. These data are then used in the Training Model and enable hypothesis testing to make further improvement to the system, evaluate compliance officer quality and compliance questionnaire and task procedural instruction material quality.

Training Model

Under the Training Model, the system's trainer module receives the data collected from the execution of the Task objects under the Subject Model and the Domain Knowledge for making decisions on the compliance questionnaire and task procedural instruction delivery strategy and providing feedbacks to the subject and compliance officer. The system for administering, evaluating, and monitoring a subject's compliance with task performance requirements within an action programme comprises a trainer module implemented by a combination of software and firmware executed in general purposed and specially designed computer processors. In one embodiment, the trainer module resides in one or more server computers. The trainer module is primarily responsible for executing the machine instructions corresponding to the carrying-out of the activities under the Training Model. Under the Training Model, the trainer module executes the followings:

1.) Define the entry points for the Tasks execution. Initially all indicators for Concept Knowledge and Skill items are set to defaults, which are inferred from data in either an application form filled by the subject or compliance officer or an initial assessment of the subject by the compliance officer. Select the subsequent Task to execute. To select the next Task, the system's trainer module searches through a logical tree data structure of Concept objects (Knowledge Tree), locate a Concept Knowledge and Skill with the lowest skill level (closest to the root of the Knowledge Tree) and then use a matching matrix to lookup the corresponding Task object for making the selection. Once selected, the Task object data is retrieved from the Domain Knowledge repository, and send to the system's communication module for delivery presentation.

2.) Provide feedback. While the subject is working on a Task object being executed, the system's trainer module monitors the time spent on a Task step. When a time limit is exceeded, feedback is provided as a function of the current affective state of the subject. For example, this can be an encouraging, empathetic, or challenging message selected from a generic list, or it is a dedicated hint from the Domain Knowledge.

3.) Drive the system's pedagogical agent. The system's trainer module matches the current affective state of the subject with the available states in the pedagogical agent. Besides providing the affective state information, text messages can be sent to the system's communication module for rendering along with the pedagogical agent's action in a user interface displayed to the subject.

4.) Decide when a Concept is mastered. As described earlier, under the Subject Model, the system estimates the probability of the subject achieving a target compliance level in a task associated with the task performance specification materials in each Concept. Based on a predetermined threshold (e.g. 95%), the compliance officer can decide when a Concept is mastered.

In accordance to various embodiments, the system for administering, evaluating, and monitoring a subject's compliance with task performance requirements within an action programme further comprises a communication module implemented by a combination of software and firmware executed in general purposed and specially designed computer processors. In one embodiment, one part of the communication module resides and is executed in one or more server computers, and other part of the communication module resides and is executed in one or more client computers including, but not limited to, desktop computers, laptop computers, tablet computers, smartphones, and other mobile computing devices, among which some are dedicated for use by the subjects and others by compliance officer.

The communication module comprises one or more user interfaces designed to present relevant data from the Domain Knowledge and materials generated by the system operating under the Subject Model and Training Model to the subjects and the compliance officers. The user interfaces are further designed to facilitate user interactions in capturing user input (textual, gesture, image, and video inputs) and displaying feedback including textual hints and the simulated pedagogical agent's actions. Another important feature of the communication module is to provide an on-screen (the screen of the computing device used by a subject) planar coordinates and size of a visual cue or focal point for the current Task object being executed. For a non-limiting example, when an operation note from a Task object is being displayed on screen, the communication module provides the planar coordinates and size of the operation note display area and this information is used to match with the collected data from a point-of-gaze tracking sensor in order to determine whether the subject is actually engaged in the Task (looking at the operation note).

Figure 2:
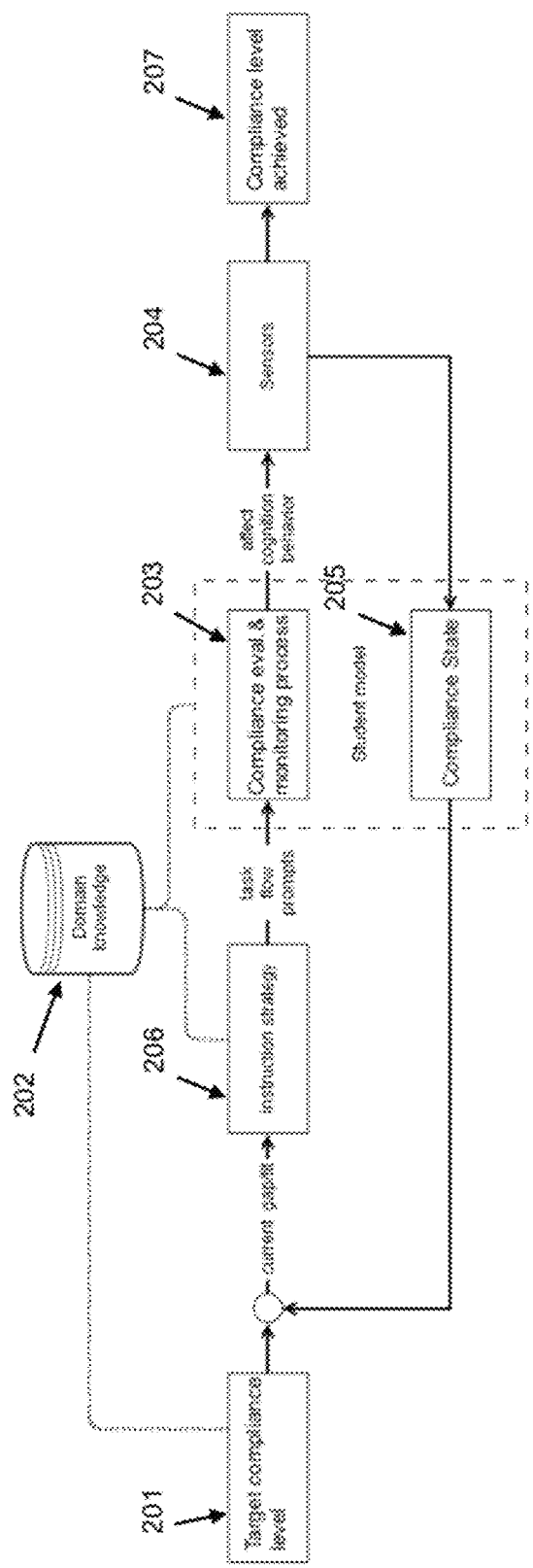
FIG. 2 depicts a logical data flow diagram of the system.

FIG. 2 depicts a logical data flow diagram of the system for administering, evaluating, and monitoring a subject's compliance with task performance requirements within an action programme in accordance to various embodiments of the present invention. The logical data flow diagram illustrates how the major components of the system work together in a feedback loop in the execution during the Subject Model and Training Model. In an exemplary embodiment in reference to FIG. 2, during enrollment, a suitable series of tasks is selected by the subject in an action programme. This series of tasks corresponds directly to a Curriculum object, which is a set of linked Concept objects in the Domain Knowledge 202, and constitutes the target compliance level 201 for this subject. Upon the subject logging into the system via a user interface rendered by the system's communication module, under the Training Model, the system's trainer module selects and retrieves from the Domain Knowledge 202 a suitable Concept object and the associated first Task object. Entering the Subject Model, the Task object data is retrieved from the Domain Knowledge repository, the system renders the Task object data (e.g. operation notes) on the user interface for the subject, and the subject starts working on the task. Meanwhile, the system manages the compliance evaluation and monitoring process 203 by collecting affective state sensory data including, but not limited to, point-of-gaze, emotion, and physiologic data, and cognition state data via Task questions and answers and the subject's behavioral-analyzing interactions with the user interface (204). After analyzing the collected affective state sensory data and cognition state data, the compliance state 205 is updated. The updated compliance state 205 is compared with the target compliance level 201. The determined knowledge/skill gap or the fit of the task procedural instruction delivery strategy 206 is provided to the Training Model again, completing the loop. If the analysis on the collected affective state sensory data and cognition state data shows a probability of achieving certain compliance level that is higher than a threshold, that certain compliance level is considered achieved 207.

Figure 3:
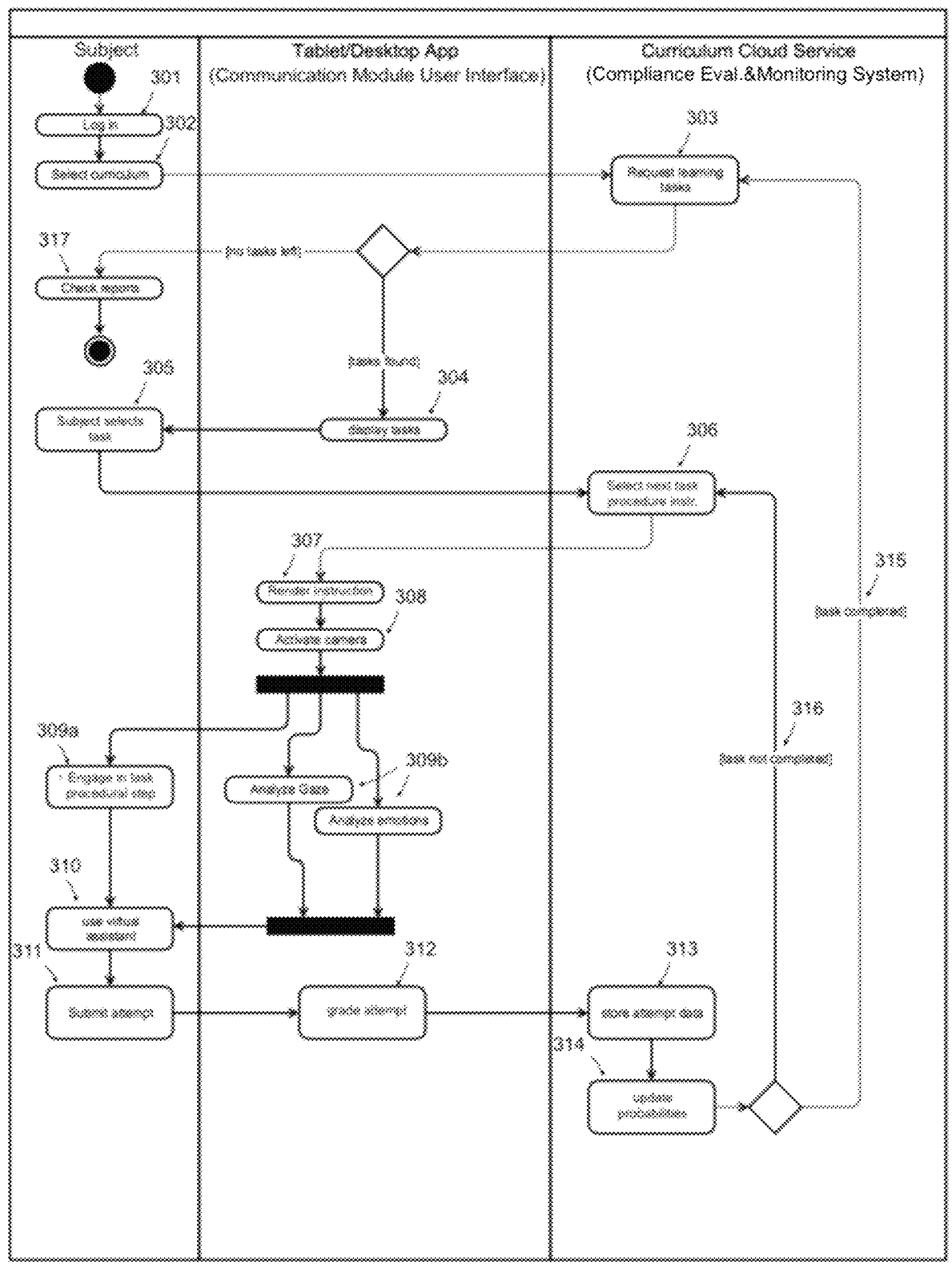
FIG. 3 depicts an activity diagram of a method for administering, evaluating, and monitoring a subject's compliance with task performance requirements within an action programme to one embodiment of the present invention.

FIG. 3 depicts an activity diagram illustrating in more details the execution process of the system for administering, evaluating, and monitoring a subject's compliance with task performance requirements within an action programme under the Subject Model and Training Model. In an exemplary embodiment referring to FIG. 3, the execution process is as follows:

301. A subject logs into the system via her computing device running a user interface rendered by the system's communication module.

302. The subject select a Curriculum presented to her in the user interface.

303. Upon receiving the user login, successful authentication, and receiving the Curriculum selection, the system's trainer module, running in a server computer, selects and requests from the Domain Knowledge repository one or more Task objects associated with the Curriculum selected. When no Task object has yet been defined to associate with any Concept objects in the Curriculum selected, the system evaluates the Knowledge Tree and finds the Concept Knowledge and Skills that the subject has not yet learned and/or been evaluated as close to the root (fundamental) of the Knowledge Tree as possible. This process is executed by the system's recommendation engine, which can be implemented by a combination of software and firmware executed in general purposed and specially designed computer processors. The recommendation engine can recommend Practice Tasks, and at lower rate Mastery Challenge Tasks. System-recommended Tasks have a default priority; compliance officer-assigned Tasks have a higher priority in the Task selection. In one embodiment, the system further comprises a recommendation engine for recommending the task performance specification materials (e.g. topic) to be learned next in a Curriculum. Using the estimated affective state and cognitive state data of the subject, performance data of the subject, the Knowledge Tree (with all 'edge' topics listed), the compliance officer's recommendation information, data from collaborative filters (look at data from peer subjects), and task performance specification content data (match subject attributes with the task performance specification material's attributes), the recommendation engine recommends the next Task to be executed by the system under the Training Model. For example, the subject's negative emotion can be eased by recognizing the difficult/unfamiliar topics (from the affective state data estimated during the execution of certain Task) and recommending the next Task of a different/more familiar topic; and recommending the next Task of a difficult/unfamiliar topic when subject's emotion state is detected position. In another example, the recommendation engine can select the next Task of higher difficulty when the estimated affective state data shows that the subject is unchallenged. This allows the matching of Tasks with the highest compliance level gains. This allows the clustering of Tasks based on similar performance data and/or affective state and cognitive state estimation. This also allows the matching of subject peers with similar compliance level accomplishment to form focus groups.

304. If the requested Task objects are found, their data are retrieved and are sent to the subject's computing device for presentation in the system's communication module user interface.

305. The subject selects a Task object to begin the compliance evaluation and monitoring session.

306. The system's trainer module retrieves from the Domain Knowledge repository the next item in the selected Task object for rendering in the system's communication module user interface.

307. Entering the Subject Model, the system's communication module user interface renders the item (compliance questionnaire question and/or task procedure instruction) in the selected Task object.

308. A camera for capturing the subject's face is activated.

309. During the subject's engagement in task procedure materials in the item in the selected Task object (309*a*), the subject's point-of-gaze and facial expressions are analyzed (309*b*).

310. Depending on the estimated affective state and cognitive state of the subject based on sensory data collected and information in the subject's profile (overlay, includes all past performance data and compliance level achievement progress data), virtual assistant may be presented in the form of guidance and/or textual hint displayed in the system's communication module user interface.

311. The subject submits an attempt answer and/or an attempt command for completing a task procedural step.

312. The attempt answer and/or attempt command is graded and the grade is displayed to the subject in the system's communication module user interface.

313. The attempt answer and/or attempt command and grade is also stored by the system for further analysis.

314. The attempt answer and/or attempt command and grade are used in calculating the probability of the subject's understanding of the Concept associated with the selected Task object and the probability of the subject achieving a target compliance level in the task.

315. If the selected Task is completed, the system's trainer module selects and requests the next Task based on the calculated probability of the subject's understanding of the associated Concept and the probability of the subject achieving a target compliance level in the task, and repeat the steps from step 303.

316. If the selected Task is not yet completed, the system's trainer module retrieves the next item in the selected Task and repeat the steps from step 306.

317. After all Tasks are completed, the system generates the result report for subject.

In accordance to another aspect of the present invention, the system for administering, evaluating, and monitoring a subject's compliance with task performance requirements within an action programme further comprises an administration module that takes information from the compliance officers, subjects, and Domain Knowledge in offering assistance with the operation of face-to-face compliance evaluation and monitoring process across multiple physical facilities as well as online, remote evaluation and monitoring. In an exemplary embodiment, the administration module comprises a constraint-based scheduling algorithm that determines the optimal scheduling of compliance evaluation and monitoring sessions while observing constraints such compliance officers' certification, travelling distance for subjects and compliance officers, first-come-first-served, composition of the compliance officers group based on compliance level achievement progress and training strategy. For example, when the compliance officer wants to promote peer teaching/training, the scheduling algorithm can select subjects with complementary skill sets so that they can help each other and form focus groups.

An in-person face-to-face compliance evaluation and monitoring session may comprise a typical flow such as: subjects check in, perform a small task to evaluate the cognitive state of the subjects, and the results are presented on the compliance officer's user interface dashboard directly after completion. The session then continues with explanation of a new task performance specification by the compliance officer, here the compliance officer receives assistance from the system's pedagogical agent with pedagogical goals and hints. After the explanation, the subjects may engage in the new task in which the system provides as much scaffolding as needed. Based on the compliance level achievement progress and affective states of the subjects, the system's trainer module decides how to continue the compliance evaluation and monitoring session with a few options: e.g. recommend to form focus groups each with subjects who have achieved similar compliance levels in prior tasks completed. The compliance evaluation and monitoring session is concluded by checking out. The attendance data is collected for billing purposes and for compliance certification purposes.

Although the embodiments of the present invention described above are primarily applied in commercial and industrial activities, surveying, and job performance assessment settings, the present invention can be adapted without undue experimentation to customer relationship management (CRM) action programmes. In accordance to one embodiment of the present invention, the method and system for administering, evaluating, and monitoring a subject's compliance with task performance requirements within an action programme comprise a mechanism for delivering and managing interactive and adaptive compliance questionnaire and task procedural instructions. The mechanism logically structures compliance questionnaire and task procedural instruction materials and the delivery mechanism data in a compliance programme as a Domain Knowledge, with its constituent Concept objects and Task objects having Knowledge and Skill items, and training materials respectively that are relevant to the concerned industry or trade. In the application of surveying, the system's estimation of the subjects' affective states and cognitive states can be used in driving the selection and presentment of survey questions. This in turn enables more accurate and speedy survey results procurements from the subjects. In the application of job performance assessment, the system's estimation of the employee subjects' affective states and cognitive states on duty continuously allows an employer to gauge the skill levels, engagement levels, and interests of the employees and in turn provides assistance in work and role assignments.

Figure 6A:
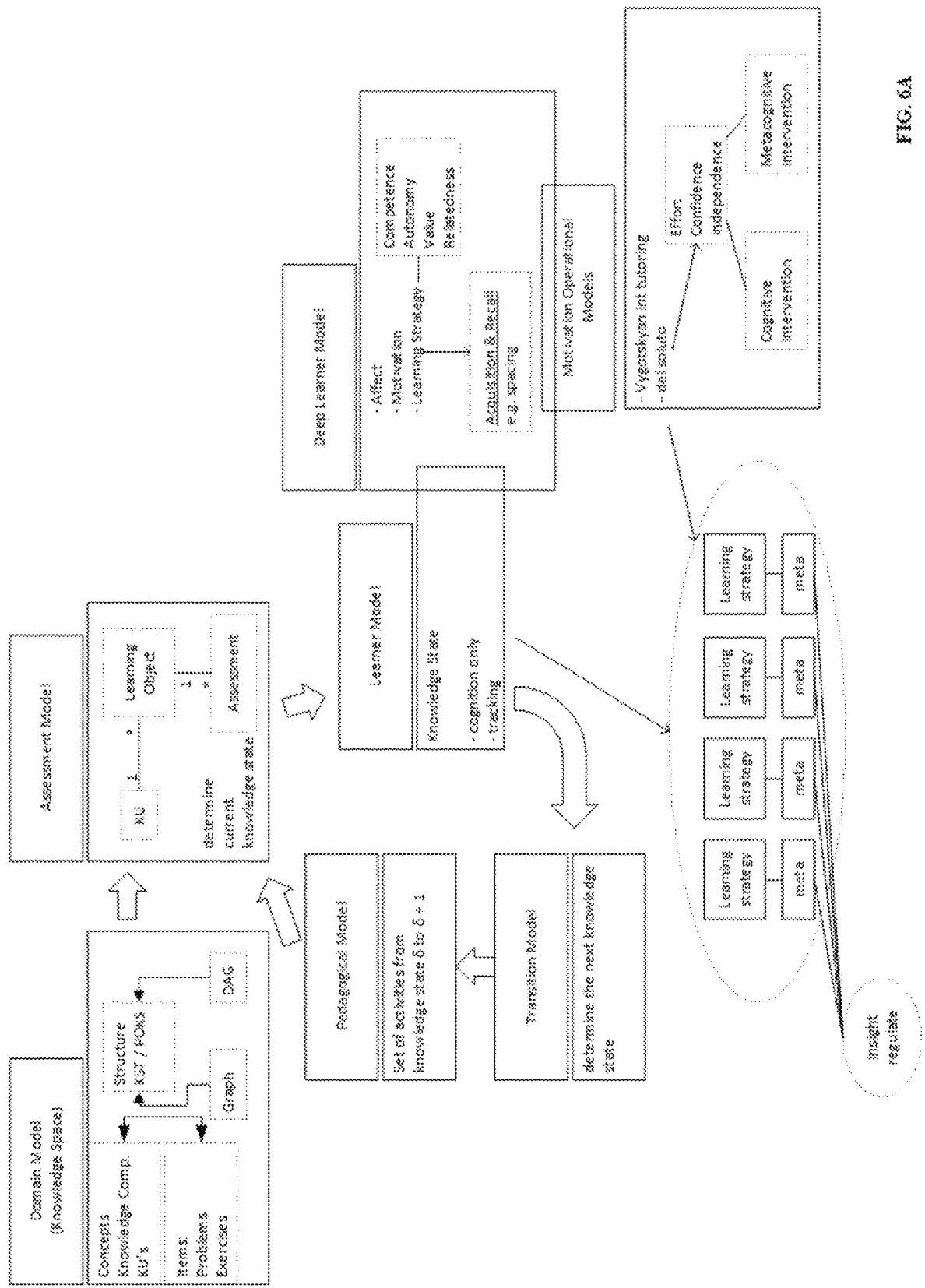
FIG. 6A depicts a logical block diagram of interlinking models of execution in accordance to one aspect of the present invention.
Figure 6B:
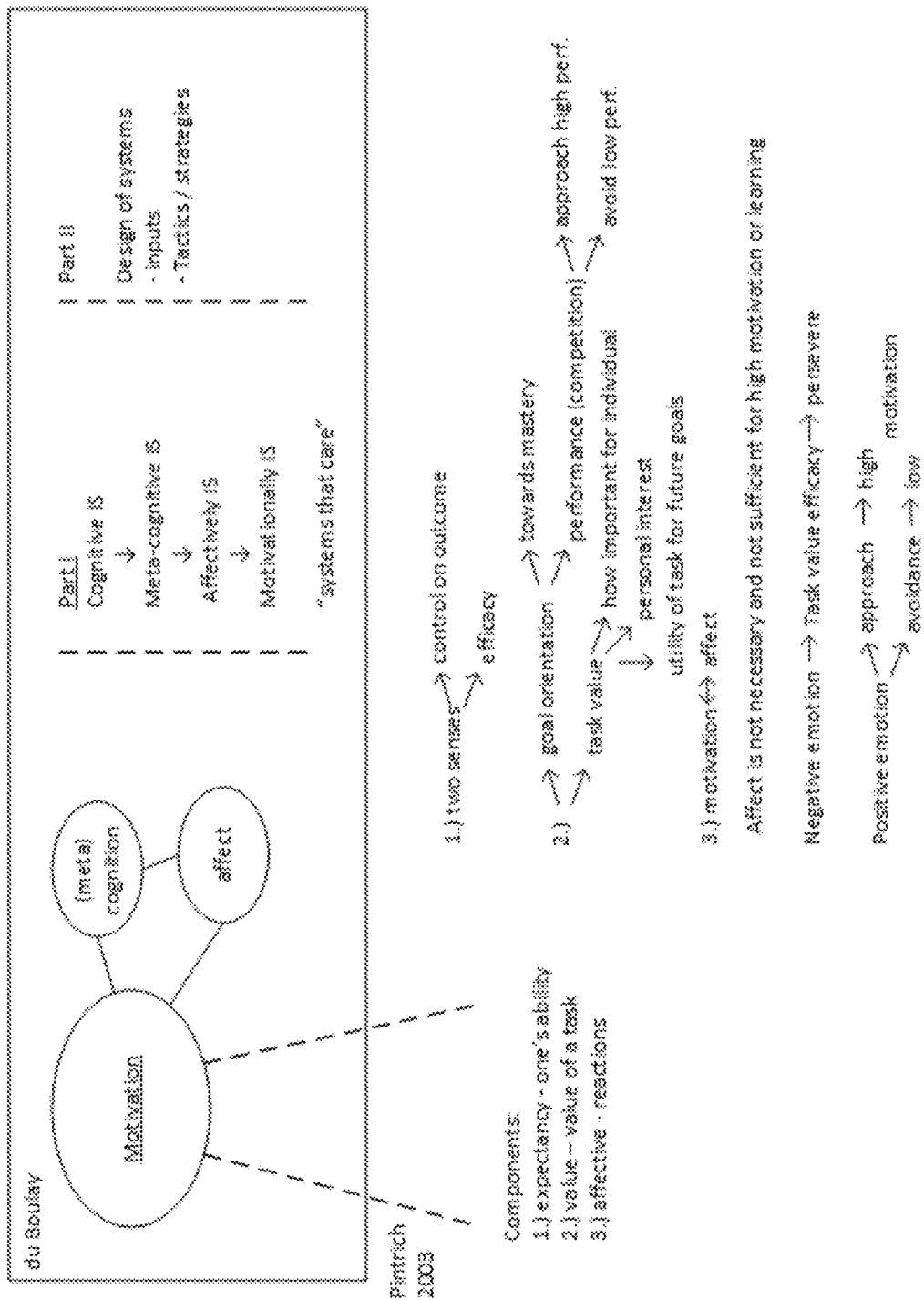
FIG. 6B shows the logical components details of the interlinking models of execution.

Referring to FIGS. 6A and 6B. In accordance to another aspect of the present invention, the method and system for method and system for administering, evaluating, and monitoring a subject's compliance with task performance requirements within an action programme incorporate machine learning techniques that are based on interlinking models of execution comprising: a Domain Model, an Assessment Model, a Learner Model, a Deep Learner Model, one or more Motivational Models, a Transition Model, and a Pedagogical Model. The interlinking models of execution is purposed for driving, inducing, or motivating certain desirable actions, behavior, and/or outcome from the subject. These certain desirable actions and/or outcome can be, as non-limiting examples, learning certain subject matters, achieving certain academic goals, achieving certain career goals, completing certain job assignments, making certain purchases, and conducting certain commercial activities. These interlinking models of execution together form a machine learning feedback loop comprising the continuous tracking and assessment of learning progress of the subject under the Assessment Model, driving the learning activities under the Learner Model, motivating the subject under the Deep Learner Model and Motivation Operational Model, and selecting and re-selecting knowledge space items under the Domain Model and Transition Model, and delivering the knowledge space items and activities from one knowledge state to the next under the Pedagogical Model.

The electronic embodiments disclosed herein may be implemented using general purpose or specialized computing devices, computer processors, or electronic circuitries including but not limited to application specific integrated circuits (ASIC), field programmable gate arrays (FPGA), and other programmable logic devices configured or programmed according to the teachings of the present disclosure. Computer instructions or software codes running in the general purpose or specialized computing devices, computer processors, or programmable logic devices can readily be prepared by practitioners skilled in the software or electronic art based on the teachings of the present disclosure.

All or portions of the electronic embodiments may be executed in one or more general purpose or computing devices including server computers, personal computers, laptop computers, mobile computing devices such as smartphones and tablet computers.

The electronic embodiments include computer storage media having computer instructions or software codes stored therein which can be used to program computers or microprocessors to perform any of the processes of the present invention. The storage media can include, but are not limited to, floppy disks, optical discs, Blu-ray Disc, DVD, CD-ROMs, and magneto-optical disks, ROMs, RAMs, flash memory devices, or any type of media or devices suitable for storing instructions, codes, and/or data.

Various embodiments of the present invention also may be implemented in distributed computing environments and/or Cloud computing environments, wherein the whole or portions of machine instructions are executed in distributed fashion by one or more processing devices interconnected by a communication network, such as an intranet, Wide Area Network (WAN), Local Area Network (LAN), the Internet, and other forms of data transmission medium.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated.

What is claimed is:

1. A system for administering, evaluating, and monitoring a subject's compliance with task performance requirements within an action programme comprising:
   one or more optical sensors configured for capturing and generating sensory data on a subject during a compliance evaluation and monitoring session;
   one or more electronic databases including one or more domain knowledge data entities, each domain knowledge data entity comprising one or more concept data entities and one or more task data entities, wherein each concept data entity comprises one or more and task performance specification content items, wherein each task data entity comprises one or more compliance questionnaire and task procedural instruction material items, wherein each task data entity is associated with at least one concept data entity, and wherein a curriculum is formed by grouping a plurality of the concept data entities;
   a subject module executed by one or more computer processing devices configured to estimate the subject's affective state and cognitive state using the sensory data collected from the optical sensors;
   a trainer module executed by one or more computer processing devices configured to select a subsequent task data entity and retrieve from the electronic databases the task data entity's compliance questionnaire and task procedural instruction material items for delivery and presentment to the subject after each completion of a task data entity in the compliance evaluation and monitoring session; and a recommendation engine executed by one or more computer processing devices configured to create a list of task data entities available for selection of the subsequent task data entity, wherein the task data entities available for selection are the task data entities associated with the one or more concept data entities forming the curriculum selected;

wherein the selection of a task data entity from the list of task data entities available for selection is based on a probability of the subject achieving a target compliance level in a task associated with the concept data entity's task performance specification content items; and wherein the probability of the subject achieving the target compliance level is computed using input data of the estimation of the subject's affective state and cognitive state.

2. The system of claim 1, further comprising:

one or more physiologic measuring devices configured for capturing one or more of the subject's tactile pressure exerted on a tactile sensing device, heart rate, electro dermal activity (EDA), skin temperature, and touch response, and generating additional sensory data during the compliance evaluation and monitoring session;

wherein the subject module is further configured to estimate the subject's affective state and cognitive state using the sensory data collected from the optical sensors and the additional sensory data collected from the physiologic measuring devices.

3. The system of claim 1, further comprising:

one or more voice recording devices configured for capturing the subject's voice and speech clarity, and generating additional sensory data during the compliance evaluation and monitoring session;

wherein the subject module is further configured to estimate the subject's affective state and cognitive state using the sensory data collected from the optical sensors and the additional sensory data collected from the voice recording devices.

4. The system of claim 1, further comprising:

one or more handwriting capturing devices configured for capturing the subject's handwriting, and generating additional sensory data during the compliance evaluation and monitoring session;

wherein the module is further configured to estimate the subject's affective state and cognitive state using the sensory data collected from the optical sensors and the additional sensory data collected from the handwriting capturing devices.

5. The system of claim 1, further comprising:

one or more pedagogical agents configured for capturing the subject's interaction with the pedagogical agents, and generating additional sensory data during the compliance evaluation and monitoring session;

wherein the module is further configured to estimate the subject's affective state and cognitive state using the sensory data collected from the optical sensors and the additional sensory data collected from the pedagogical agents.

6. The system of claim 1, wherein each of the task performance specification content material items is an operation note, an illustration, a test question, a video with an embedded test question, a problem-solving exercise having multiple steps designed to provide guidance in deriving a solution to a problem, or a problem-solving exercise having one or more heuristic rules or constraints for simulating problem-solving exercise steps delivered in synchronous with the subject's performance of the task procedural steps associated with the task performance specification.

7. The system of claim 1, wherein a plurality of the concept data entities are linked to form a logical tree data structure;

wherein concept data entities having knowledge and skill content items that are fundamental in a topic are represented by nodes closer to a root of the logical tree data structure and concept data entities having knowledge and skill content items that are advance and branches of a common fundamental knowledge and skill content item are represented by nodes higher up in different branches of the logical tree data structure;

wherein the recommendation engine is further configured to create a list of task data entities available for selection of the subsequent task data entity, wherein the task data entities available for selection are the task data entities associated with the one or more concept data entities forming the curriculum selected and the one or more concept data entities having knowledge and skill items not yet mastered by the subject and as close to the roots of the logical tree data structures that the concept data entities belonging to.

8. The system of claim 1, wherein the probability of the subject achieving the target compliance level is computed using input data of the estimation the subject's affective state and cognitive state and the subject's performance data and behavioral data; and wherein the subject's performance data and behavioral data comprises one or more of number of successful and unsuccessful attempts to task procedural step completions, speed in completing task procedures, correctness of answers to questions in the questionnaire, number of successful and unsuccessful attempts to questions, closeness of the subject's answers to model answers, toggling between given answer choices, and response speed to test questions of certain types, subject matters, and/or task performance specification complexity/difficulty/stringency levels, working steps toward a solution, the subject's handwriting, tone of voice, and speech clarity.

9. The system of claim 1, wherein the sensory data comprises one or more of the subject's facial expression, eye movements, point-of-gaze, and head pose.

10. The system of claim 1, wherein the selection of a task data entity from the list of task data entities available for selection is based on the probability of the subject achieving the target compliance level and the subject's estimated affective state;

wherein when the subject's estimated affective state indicates a negative emotion, a task data entity that is associated with a concept data entity having knowledge and skill content items that are favored by the subject is selected over another task data entity that is associated with another concept data entity having knowledge and skill content items that are disliked by the subject; and wherein when the subject's estimated affective state indicates a positive emotion, a task data entity that is associated with a concept data entity having knowledge and skill content items that are disliked by the subject is selected over another task data entity that is associated with another concept data entity having knowledge and skill content items that are favored by the subject.

11. A method for administering, evaluating, and monitoring a subject's compliance with task performance requirements within an action programme comprising:
- capturing and generating sensory data on a subject using one or more optical sensors during the compliance evaluation and monitoring session;
- providing one or more electronic databases including one or more domain knowledge data entities, each domain knowledge data entity comprising one or more concept data entities and one or more task data entities, wherein each concept data entity comprises one or more task performance specification content items, wherein each task data entity comprises one or more compliance questionnaire and task procedural instruction material items, wherein each task data entity is associated with at least one concept data entity, and wherein a curriculum is formed by grouping a plurality of the concept data entities;
- estimating the subject's affective state and cognitive state using the sensory data collected from the optical sensors; and
- selecting a subsequent task data entity and retrieving from the electronic databases the task data entity's compliance questionnaire and task procedural instruction material items for delivery and presentment to the subject after each completion of a task data entity in the compliance evaluation and monitoring session;
- creating a list of task data entities available for selection of the subsequent task data entity, wherein the task data entities available for selection are the task data entities associated with the one or more concept data entities forming the curriculum selected;
- wherein the selection of a task data entity from the list of task data entities available for selection is based on a probability of the subject achieving a target compliance level in a task associated with the concept data entity's task performance specification content items; and
- wherein the probability of the subject achieving the target compliance is computed using input data of the estimation of the subject's affective state and cognitive state.

12. The method of claim 11, further comprising:
- capturing and generating additional sensory data on one or more of the subject's tactile pressure exerted on a tactile sensing device, heart rate, electro dermal activity (EDA), skin temperature, and touch response during the compliance evaluation and monitoring session;
- wherein the estimation of the subject's affective state and cognitive state uses the sensory data collected from the optical sensors and the additional sensory data.

13. The method of claim 11, further comprising:
- capturing and generating additional sensory data on the subject's voice and speech clarity using one or more voice recording devices during the compliance evaluation and monitoring session;
- wherein the estimation of the subject's affective state and cognitive state uses the sensory data collected from the optical sensors and the additional sensory data collected from the voice recording devices.

14. The method of claim 11, further comprising:
- capturing and generating additional sensory data on the subject's handwriting using one or more handwriting capturing devices during the compliance evaluation and monitoring session;
- wherein the estimation of the subject's affective state and cognitive state uses the sensory data collected from the optical sensors and the additional sensory data collected from the handwriting capturing devices.

15. The method of claim 11, further comprising:
- capturing and generating additional sensory data on the subject's interaction with one or more pedagogical agents during the compliance evaluation and monitoring session;
- wherein the estimation of the subject's affective state and cognitive state uses the sensory data collected from the optical sensors and the additional sensory data collected from the pedagogical agents.

16. The method of claim 11, wherein each of the task performance specification content material items is an operation note, an illustration, a test question, a video with an embedded test question, a problem-solving exercise having multiple steps designed to provide guidance in deriving a solution to a problem, or a problem-solving exercise having one or more heuristic rules or constraints for simulating problem-solving exercise steps delivered in synchronous with the subject's performance of the task procedural steps associated with the task performance specification.

17. The method of claim 11,
- wherein a plurality of the concept data entities are linked to form a logical tree data structure;
- wherein concept data entities having knowledge and skill content items that are fundamental in a topic are represented by nodes closer to a root of the logical tree data structure and concept data entities having knowledge and skill content items that are advance and branches of a common fundamental knowledge and skill content item are represented by nodes higher up in different branches of the logical tree data structure;
- wherein the task data entities available for selection are the task data entities associated with the one or more concept data entities forming the curriculum selected and the one or more concept data entities having knowledge and skill items not yet mastered by the subject and as close to the roots of the logical tree data structures that the concept data entities belonging to.

18. The method of claim 11,
- wherein the probability of the subject achieving a target compliance level is computed using input data of the estimation the subject's affective state and cognitive state and the subject's performance data and behavioral data; and
- wherein the subject's performance data and behavioral data comprises one or more of number of successful and unsuccessful attempts to task procedural step completions, speed in completing task procedures, correctness of answers to questions in the questionnaire, number of successful and unsuccessful attempts to questions, closeness of the subject's answers to model answers, toggling between given answer choices, and response speed to test questions of certain types, subject matters, and/or task performance specification complexity/difficulty/stringency levels, working steps toward a solution, the subject's handwriting, tone of voice, and speech clarity.

19. The method of claim 11, wherein the sensory data comprises one or more of the subject's facial expression, eye movements, point-of-gaze, and head pose.

20. The method of claim 11,
- wherein the selection of a task data entity from the list of task data entities available for selection is based on the probability of the subject achieving the target compliance level and the subject's estimated affective state;

wherein when the subject's estimated affective state indicates a negative emotion, a task data entity that is associated with a concept data entity having knowledge and skill content items that are favored by the subject is selected over another task data entity that is associated with another concept data entity having knowledge and skill content items that are disliked by the subject; and wherein when the subject's estimated affective state indicates a positive emotion, a task data entity that is associated with a concept data entity having knowledge and skill content items that are disliked by the subject is selected over another task data entity that is associated with another concept data entity having knowledge and skill content items that are favored by the subject.

* * * * *